Figure 1:
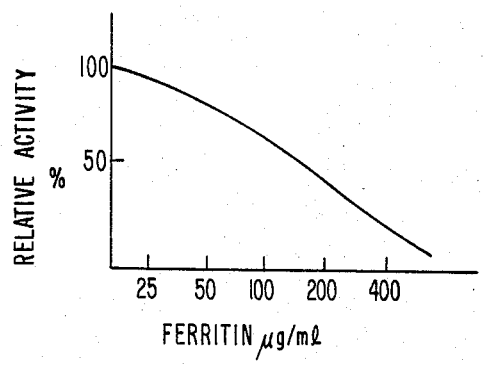

United States Patent [19]

Kasahara et al.

[11] Patent Number: 4,582,792

[45] Date of Patent: Apr. 15, 1986

[54] IMMUNOASSAY METHOD USING TWO IMMOBILIZED BIOLOGICALLY ACTIVE SUBSTANCES

[75] Inventors: Yasushi Kasahara; Hiromasa Suzuki; Yoshihiro Ashihara, all of Tokyo, Japan

[73] Assignee: Fujirebio Kabushiki Kaisha, Tokyo, Japan

[21] Appl. No.: 491,661

[22] Filed: May 5, 1983

[30] Foreign Application Priority Data

May 10, 1982 [JP] Japan .................................. 57-76678

[51] Int. Cl.$^4$ .................... G01N 33/54; G01N 33/543; G01N 33/546; G01N 33/545
[52] U.S. Cl. ......................................... 435/7; 436/523; 436/531; 436/533; 436/810
[58] Field of Search ..................... 435/7; 436/523, 531, 436/532, 810, 823, 824, 533, 534

[56] References Cited

U.S. PATENT DOCUMENTS

| | | | |
|---|---|---|---|
| 4,225,575 | 10/1980 | Plasio | 436/531 X |
| 4,279,617 | 7/1981 | Masson | 435/7 X |
| 4,294,817 | 10/1981 | Burgett | 435/7 X |
| 4,305,925 | 12/1981 | Kapmeyer | 436/523 X |
| 4,378,344 | 3/1983 | Zahradnik | 435/7 X |
| 4,416,813 | 11/1983 | Ikeda | 435/7 X |
| 4,435,504 | 3/1984 | Zuk | 435/7 |
| 4,459,361 | 7/1984 | Gefter | 436/523 |

Primary Examiner—Sidney Marantz
Assistant Examiner—Jeremy Jay
Attorney, Agent, or Firm—Burgess, Ryan & Wayne

[57] ABSTRACT

A biologically active composition comprising an immobilized phase comprising an antigen or an antibody, and an immobilized phase comprising an enzyme, an enzyme inhibitor or activator, and a method of measuring antigen or antibody using the same. According to the method of the invention, antigen with antibody can be detected in a simple procedure and high sensitivity.

18 Claims, 5 Drawing Figures

IMMUNOASSAY METHOD USING TWO IMMOBILIZED BIOLOGICALLY ACTIVE SUBSTANCES

This invention relates to a biologically active composition wherein two biologically active substances are separately immobilized, and a method of measuring antigen and antibody using the same.

Various methods of measuring antigen and antibody have been developed, and among them, enzyme immunoassay is widely employed because of its improved specificity, sensitivity, simplicity operation and simplicity apparatus. At present, various improvements have been investigated in order to simplify the operation and improve the sensitivity.

It is an object of the present invention to provide a novel biologically active composition where two kinds of biologically active substances are separately immobilized. It is another object of the present invention to provide a novel enzyme immunoassay using the above biologically active composition, involving a simple procedure capable of detecting antigen or antibody in high sensitivity.

The biologically active composition comprises an immobilization phase of an antigen or an antibody and an immobilization phase of an enzyme or an enzyme inhibitor or activator.

The kinds of the antigen and the antibody to be immobilized are not limited and are selected according to the use of this biologically active composition. The antigen includes haptens and first antibodies in the case of double antibody method. The antibody includes the digestion products of an immunoglobulin with protease such as F(ab')$_2$, Fab' and Fab, and second antibodies against first antibodies. Moreover, all combinations of an antigen, a first antibody and a second antibody in the case of the double antibody method, may be employed as a combination of the antigen and the antibody of the present invention. Such antigen and antibody include the antigens and the antibodies existing in organs, blood and urine, such as hormones derived from various endocrine glands, proteins in blood serum such as immunoglobulins, albumins and ferritins, immune complexes, pathogens such as HB antigen, complements, drugs such as digoxin, cyclic nucleotides, α-fetoproteins, and carcinoembryonic antigens.

The enzyme and the enzyme inhibitor or activator react with each other. Examples of such combination include an α-amylase and an amylase inhibitor, a β-galactosidase and an isoflavonoid, and an esterase and a bestatin.

Since the antigen or the antibody and the enzyme or the enzyme inhibitor or activator are immobilized on one or more carriers there are four kinds of combinations which are the antigen and the enzyme, the antigen and the enzyme inhibitor or activator, the antibody and the enzyme, and the antibody and the enyzme inhibitor or activator.

Such a biologically active composition is characterized by the separate immobilization on a carrier of the antigen or the antibody separately from the enzyme or the enzyme activator or inhibitor. That is, when the combination material described later reacts and combines with a immobilized phase, the combination material cannot combine with the second immobilized phase. However, of course, the combination material may react with both immobilized phases at the boundary region.

Specifically such a solid biologically active composition includes a polymer material on which an antigen or an antibody and an enzyme or an enzyme inhibitor or activator are immobilized at different parts of the same polymer. It also includes two polymer materials which are stuck to each other and on one of which an antigen or an antibody is immobilized and on the other of which an enzyme or an enzyme inhibitor or activator is immobilized. Other than the above, in the case of a considerably large particle, as, for example, one having a diameter of more than 3 mm, since the contacting area between particles is minor in comparison with the total surface area, the above biologically active composition may consist of a mixture of two particle groups. Namely, on the particles belonging to one group, an antigen or an antibody is immobilized, and on the particles belonging to the other group, an enzyme or an enzyme inhibitor or activator is immobilized.

Among the above compositions, in the case of a polymer material on which two kinds of the biologically active substances are immobilized at different parts of the same polymer, the polymer material may be produced by using a block-copolymer or a graft-copolymer. In this case, an antigen or an antibody and an enzyme or an enzyme inhibitor or activator are separately immobilized by using the different functional groups of the copolymer. Functional groups, such as —NH$_2$, —COOH, —CHO, —OH and —SH may be used. In the case where the biologically active substances such as an antigen or an enzyme inhibitor do not lose their activity through the copolymerization reaction, they may be immobilized by coupling to the monomers or block polymers before the copolymerization. In such a case, the functional groups of the comonomers of block polymers may be identical.

In the case of the two polymer materials which are stuck to each other, the immobilization of the biologically active substances may be carried out before or after the sticking. The sticking may be carried out by welding or pasting.

The shape of the composition includes a sphere, a disk, a cube or a ring.

The immobilization may be carried out according to the known methods. A biologically active protein material may be immobilized by using the known method of immobilizing a biologically active protein such as an enzyme. Known methods include the covalently bound method such as the diazotization methods, the peptide synthesis method and the alkylation method, the ionic bond method and the physical adsorption method. In the case of other than the protein material, a suitable method is selected by considering the functional group of the biologically active substance and that of the solid carrier material. The immobilized antigen includes the reaction product of an antigen and a first antibody in the case that the first antibody is allowed to react with the antigen covalently bound to a carrier material and then the reaction product is further allowed to react with a second antibody.

When an antigen is measured by using such a biologically active composition, an antibody capable of reacting with the antigen to be measured or an antigen capable of reacting with the above antibody is immobilized on a carrier material to form one immobilized phase. On the other hand, when an antibody is measured, an antigen capable of reacting with the antibody to be measured or an antibody capable of reacting with the above antigen is immobilized on the carrier material.

And, a combination matter of an antibody or an antigen capable of reacting with the immobilized antigen or antibody of the biologically active composition and an enzyme inhibitor or activator or an enzyme capable of reacting with the immobilized enzyme or enzyme inhibitor or activator and the antigen or the antibody to be measured are contacted with the above biologically active composition in an aqueous solution, and thereby the reaction between the antigen and the antibody competes with the reaction between the enzyme and the enzyme inhibitor or activator. Thereafter, the antigen or antibody can be determined by the measurement of the enzyme activity.

The above antigen or the above antibody to be measured is not limited to the object antigen or the desired antibody to be measured. For example, in the case of the double antibody method, the reaction product of the desired antigen to be measured and a first antibody is the antigen to be measured in this specification.

There are 4 couples in the case of the combination material which are an antigen and an enzyme, an antigen and an enzyme inhibitor or activator, an antibody and an enzyme, and an antibody and an enzyme inhibitor or activator. However, this combination material should react with both immobilized phases of the composition and, accordingly, this couple is determined according to the biologically active composition.

Where both materials to be combined are proteins, such a combination material may be produced according to the known cross-linking method or the peptide synthesis method to immobilize a biologically active protein such as an enzyme. Where one or both materials are not proteins, a suitable method to produce the combination material is selected by considering the functional groups of the materials to be combined.

The principle of the measurement of an antigen or antibody according to the present invention is explained by example of the case of measuring an antigen by using a biologically active composition comprising an immobilized antigen and an immobilized enzyme inhibitor and a combination material comprising an enzyme and an antibody. First, when the antigen to be measured is not present, the combination material combines with the immobilized antigen and it does not combine with the immobilized enzyme inhibitor because the binding force between the antigen and antibody is usually stronger than the binding force between the enzyme and enzyme inhibitor. On the other hand, when the antigen to be measured is present, the antibody of the combination material competitively reacts against the antigen to be measured and the immobilized antigen. And, when the combination material combines with the antigen to be measured, the enzyme portion of the combination material further reacts to combine with the immobilized enzyme inhibitor of a composition. As the result, the enzyme activity is lowered according to the combined amount and, accordingly, the amount of the antigen to be measured can be determined by measuring the lowering degree of the enzyme activity and then referring to the calibration curve indicating the relation between the amount of free antigen and the lowering degree of the enzyme activity which was previously measured.

The measurement of antigen or antibody is carried out by contacting the biologically active composition with the combination material and with the antigen or the antibody to be measured in an aqueous solution. In this case, the order of the biologically active contacting is not limited. Thus, the composition may be contacted with the combination material and the antigen or the antibody at once, or the biologically active composition may first be contacted with the either the combination material or the antigen or the antibody and then contacted with the remaining one. The measurement includes the case where the combination material of an antigen and an enzyme is allowed to react with an antibody immobilized on a tube and then the remaining combination material is scavenged by an enzyme inhibitor immobilized on a bead.

The aqueous solution may preferably be kept at a suitable pH for the reaction of antigen and antibody and for the reaction of enzyme and its inhibitor or activator, and accordingly, the use of a buffer solution such as a phosphate buffer solution, a borate buffer solution and a tris-HCl buffer solution is preferable. The suitable pH depends on the kinds of the antigen, the antibody, the enzyme and the enzyme inhibitor or activator, and it is usually in the range of pH 5 to 8. The suitable temperature of the aqueous solution is also different according to the kinds of the antigen, the antibody, the enzyme and the enzyme inhibitor or activator, and it is usually at in the range of 15° to 45° C.

After the contacting, the enzyme activity or the enzyme inhibitory or activating activity of the biologically active composition or of the aqueous solution is measured. The measurement is carried out according to the known methods, colorimetry, fluorometry, and emission spectrography using a photon counter may be employed.

The assay method of the present invention can detect various antigens and antibodies. Among the conventional methods, the sandwich method which is one of the representative methods among the enzyme immunoassay is objectionable because it is a complicated operation, and the homogeneous enzyme immunoassay which is also the representative method is objectionable because of insufficient sensitivity. Whereas, in the case of the method of the invention, its operation is a simple one and its sensitivity is sufficiently high. In the present method, the desired results are obtained by the particular technique where both the antigen or the antibody and the enzyme or the enzyme inhibitor or activator are immobilized and the immobilization phases are separated from each other. By this phase separation, the combination material of the antigen or the antibody and the enzyme or the enzyme inhibitor or activator which has combined with one immobilized phase cannot combine with the other immobilized phase. And accordingly, the high sensitivity can be achieved surprisingly, in a simple operation.

EXAMPLE 1

(1) Preparation of Biologically Active Composition

10 Grams of a dextran having an average molecular weight of 500,000 dalton (manufactured by Pharmacia Fine Chemicals) was dissolved in 50 ml of 0.1N NaOH containing 80% ethanol. 0.6 g of sodium monochloroacetate was gradually added to the solution, and allowed to react at 30° C. for 5 hours to introduce carboxymethyl groups.

After the reaction, a part of the reaction product was dialyzed against 10 mM borate buffer solution pH 6.0, and to the dialyzate, 100 pieces of spherical nylon beads 6 mm in diameter and wherein amino groups were liberated by treating with 3HCl for 24 hours were added. Water-soluble carbodiimide (hereinafter referred to as WSC) was added to the mixture, and allowed to react at 4° C. for 6 hours. The dextran was thus introduced to a part of amino groups of the nylon beads.

The beads were washed twice with the same buffer solution described above. A phenylacetoaldoxime induced amino group which is the inhibitor of $\beta$-galactosidase was dissolved in 10 mM borate buffer solution of a pH 5.5, and allowed to react with succinic anhydride. The reaction product was added to the above washed beads in a concentration of 1 mg/ml, and allowed to react at 30° C. for 18 hours in the presence of WSC. Thereby, the above inhibitor was introduced in the remaining amino groups of the nylon beads.

0.02M sodium periodate solution was added to the nylon beads, and allowed to react at 4° C. for 30 minutes. Subsequently, ethylene glycol was added in a concentration of 0.04M, and allowed to react at room temperature for 1 hour. The reaction solution was removed, and 10 $\mu$g/ml ferritin dissolved in 50 mM sodium carbonate buffer solution pH 8.5 was added to the nylon beads, and allowed to react at room temperature for 4 hours. 1 mg of sodium boro-hydride was added to the reaction mixture, and allowed to stand overnight. The nylon beads were then washed twice with the same buffer solution containing 0.5% bovine serum albumin (BSA), and preserved in 20 mM sodium phosphate buffer solution pH 7.5.

(2) Preparation of Combination Material $\beta$-D-Galactosidase prepared from hog liver was combined with antigen by the known maleimide crosslinking method.

20 mg of IgG fractin of goat anti human ferritin antibody was dissolved in 1 ml of 0.1M sodium acetate pH 4.5. 0.4 mg of pepsin was added to the solution, and the above antibody was digested at 37° C. for 16 hours. The pH of the digest was adjusted to 8.0, and the digest was introduced into a column of Sephadex G-150. Then, the adsorbates were eluted by 0.1M sodium borate buffer solution pH 8.0, and the F(ab')$_2$ fraction was separated.

This fraction was allowed to react with 20 $\mu$mole of 2-mercaptoethylamine in 0.1M sodium acetate buffer solution pH 5.0 at 37° C. for 90 minutes, and the excess reagent was removed by using a column of Sephadex G-25.

Fab' thus produced was added to 0.1M sodium acetate buffer solution pH 5.0. 1.0 ml of the saturated solution of N,N'-(1,2-phenylene)bismaleimide was added to the Fab' solution, and the mixture was allowed to react at 30° C. for 20 minutes. After the reaction, maleimide-Fab' was collected using a Sephadex G-25 column.

20 $\mu$l of $\beta$-D-galactosidase solution containing ammonium sulfate in a suspended state was added to the maleimide-Fab', and allowed to react at 30° C. for 20 minutes. The reaction mixture was neutralized and purified by a Sepharose 6B column equilibrated with 10 mM sodium phosphate buffer solution pH 7.0 containing 0.1% BSA-1 mM MgCl$_2$-1M NaCl to produce an enzyme labelled antigen.

(3) Measurement of Ferritin Antigen

One piece of the nylon bead of the biologically active composition prepared in paragraph (1) was placed in a test tube, and 0.4 ml of 0.1M phosphate buffer solution pH 7.0 was added. Subsequently, 50 $\mu$l of a ferritin standard solution or a diluted blood serum and 50 $\mu$l of diluted enzyme labelled antigen prepared as in paragraph (2) supra was added in the test tube, and allowed to react at 37° C. for 1 hour. 0.5 ml of 0.005M p-nitrophenyl-$\beta$-D-galactopyranoside was added as the substrate, and allowed to react at 37° C. for 15 minutes. 2.0 ml of 0.4M glycine-NaOH buffer solution (pH 10.5) was added to the reaction solution, and the reaction was stopped. Then, the absorbance of the reaction solution at 400 nm was measured.

The results of the relation between the concentration of ferritin and the relative activity of $\beta$-D-galactosidase of the reaction solution are shown in FIG. 1. When ferritin concentrations of various blood sera were measured by using the curve of FIG. 1 as the calibration curve, a good correlation between the results of this method and the results obtained by the conventional method (the RIA method) was obtained.

EXAMPLE 2

(1) Preparation of Biologically Active Composition 0.5 Gram of a cation-exchange resin (Amberite IRC-50) and 0.6 g of an anion-exchange resin (Amberite IR-45) were individually ground. Each powder was uniformly placed on separate polystyrene plates having about 1 cm$^2$, and adhered by pressing at 400 kg/cm$^2$.

This cation-exchange resin plate was immersed in dioxane, and 0.1M N-hydroxysuccinimide and N,N'-dicyclohexylcarbodiimide were added and reacted at room temperature for 90 minutes with stirring. The plate was washed with a small amount of methanol, and 2.5 ml of $\beta_2$-microglobulin solution diluted with 0.1M NaHCO$_3$ solution was added. Then, the mixture was allowed to react at 4° C. for 24 hours. The plate was washed with 0.05M tris buffer solution pH 8.0, and accordingly, an immobilized $\beta_2$-microglobulin plate was obtained.

On the other hand, the anion-exchange resin plate was immersed in a 50 mM sodium borate buffer solution pH 6.0 containing 10 mg/ml of aminopeptidase B prepared from a liver of a rat, and WSC was added. The mixture was allowed to react at room temperature for 2 hours. The plate was washed with the same buffer solution, and accordingly, an immobilized enzyme plate was obtained.

(2) Preparation of Combination Material

The N-Hydroxysuccinimide ester of bestatin which is the inhibitor of aminopeptidase B and separated from an actinomycete was dissolved in 0.1M NaHCO$_3$ in a concentration of 0.02 mg/ml. 10 mg of IgG fraction of goat anti human $\beta_2$-microglobulin was added to the solution, and allowed to react at room temperature for 2 hours. The reaction mixture was then separated by using a Sephadex G-25 column, and the inhibitor labelled antibody was obtained.

(3) Measurement of $\beta_2$-Microglobulin

The immobilized $\beta_2$-microglobulin plate was placed in a test tube, and 0.4 ml of 50 mM sodium phosphate buffer solution pH 7.2 containing the inhibitor labelled antibody and 0.1 ml of $\beta_2$-microglobulin standard solution or a diluted blood serum specimen were added. The mixture was then allowed to react at 37° C. for 30 minutes. 0.5 ml of 1-arginine-$\beta$-naphthylamide solution was added as the substrate, and allowed to react at 37° C. for 30 minutes. 1.0 ml of a garnet reagent was added, and allowed to stand at room temperature for 15 minutes.

Then, the absorbance of the reaction solution at 525 nm was measured.

Figure 2:
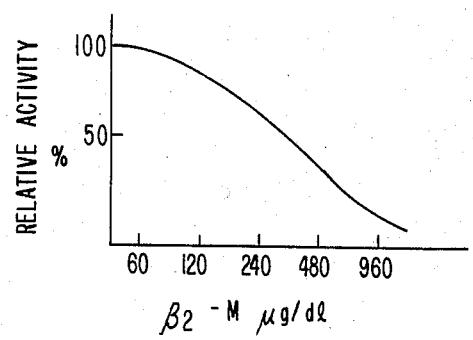

The results of the relation between the concentration of $\beta_2$-microglobulin and the relative activity of aminopeptidase B of the reaction solution are shown in FIG. 2.

EXAMPLE 3

(1) Preparation of Biologically Active Composition 20 mg of a proteinaceous amylase inhibitor obtained from wheat flour and having a molecular weight of about 24000 was dissolved in 0.1M phosphate buffer solution pH 7.5 containing 5 mM EDTA. 100 µl of 9 mg/ml S-acetylmercaptosuccinic anhydride dimethyl sulfoxide solution was added to the solution, and warmed at 37° C. for 1 hour. Subsequently, 110 µl of 1M hydroxylamine of pH 7.5 was added, and allowed to react at 37° C. for 30 minutes. The reaction mixture was introduced into a column of Sephadex G-25, and a filtration was carried out by using 0.1M phosphate buffer solution pH 6.5 containing 1 mM EDTA to remove unreacted S-acetylmercaptosuccinic acid, and accordingly an amylase inhibitor induced mercaptyl group was obtained.

On the other hand, spherical nylon beads 4 mm in diameter was treated with 3NHCl for 24 hours to liberate their amino groups. The treated nylon beads were washed with water, and immersed in 0.1M phosphate buffer solution pH 6.3. 1/10 by volume of 2 mg/ml 4-maleimido-methylcyclohexane-1-carboxylic acid succinimide ester (CHMS) dioxane solution was added, and allowed to react at room temperature for 3 hours. After the reaction, the beads were washed twice with 0.1M phosphate buffer solution pH 6.3, and the above amylase inhibitor induced mercaptyl group solution was added to the washed beads, and allowed to react at 4° C. overnight. The beads were washed with the same buffer solution as above, and preserved in 50 mM phosphate buffer solution pH 7.0 containing 1% BSA to obtain the immobilized amylase inhibitor beads.

Next, spherical polystyrene beads 3.6 mm in diameter were washed with water, and immersed in a solution of goat anti human α-fetoprotein specific IgG ($OD_{280}=0.1$) dissolved in 20 mM phosphate buffer solution pH 7.5. The mixture was allowed to stand at 4° C. for 2 days, and the above IgG was adsorbed on the beads. The beads were sufficiently washed with 20 mM phosphate buffer solution pH 7.5, and preserved in 50 mM phosphate buffer solution pH 7.5 containing 1% BSA and 0.14M sodium chloride to obtain the immobilized antibody beads.

(2) Preparation of Combination Material 5 mg of α-amylase obtained from hog pancreas was dissolved in 0.1M phosphate buffer solution pH 7.5 containing 5 mM EDTA. 100 µl of 9 mg/ml S-acetylmercaptosuccinic anhydride dimethyl sulfoxide solution was added to the solution, and warmed at 37° C. for 30 minutes. Subsequently, 110 µl of 1M hydroxylamine of pH 7.5 was added, and allowed to react at 37° C. for 30 minutes. This reaction mixture was introduced into a column of Sephadex G-25, and gel filtration was carried out by using 0.1M phosphate buffer solution pH 6.5 containing 1 mM EDTA to remove unreacted S-acetylmercaptosuccinic anhydride. α-Amylase induced mercaptyl group thus obtained was concentrated to 1 ml.

On the other hand, 1 mg of α-fetoprotein (AFP) obtained from human ascites was dissolved in 1 ml of 0.1M phosphate buffer solution pH 6.3. 100 µl of 2 mg/ml CHMS dioxane solution was added, and allowed to react at room temperature for 1 hour. This reaction mixture was introduced into a column of Sephadex G-25 (1 cm×40 cm), and gel filtration was carried out by using 0.1M phosphate buffer solution pH 6.5 containing 1 mM EDTA to remove unreacted CHMS. The combination product of 4-maleimido methylcyclohexane-1-carboxylic acid and human AFP (CHM induced AFP) solution thus produced was concentrated to 1 ml. The α-amylase induced mercaptyl group was added to this concentrate, and allowed to react at 4° C. overnight. The reaction mixture was separated by gel filtration using Sephacryl S-200 column (1 cm×120 cm), and the AFP-amylase combination material was obtained.

(3) Measurement of AFP

One piece of the immobilized amylase inhibitor beads and one of the immobilized antibody beads was placed in each test tube, and 800 µl of 50 mM tris buffer solution—0.14M NaCl—0.2M BSA pH 7.8 was added.

800 ng/ml AFP solution was prepared, and the solution was diluted to produce 4n diluted solution series.

Each 100 µl of the diluted solution and then 100 µl of the AFP-amylase combination material were added to each test tube, and allowed to stand at room temperature for one and half hours.

Subsequently, 1 ml of "Autopack α-amylase" (trade name, manufactured by Boehringer Mannheim GmbH) was added as a substrate, and the absorbance at 405 nm of the reaction solution after 10 minutes was measured.

Figure 3:
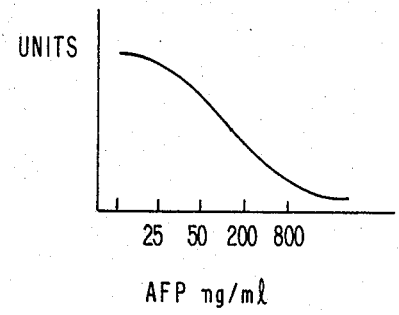

The results of the relation between the AFP concentration and the enzyme activity are shown in FIG. 3.

Next, various human sera were diluted 5 times, and using each 100 µl of the diluted sera, the measurements were carried out in the same manner as above. The AFP concentrations of each serum were determined by using the curve of FIG. 3 as the calibration curve. On the other hand, the AFP concentrations of the same sera were measured by the conventional radioimmunoassay (RIA). The results are shown in the following table.

| Serum | The method of the invention | RIA method |
|---|---|---|
| A | 50 ng/ml | 43.2 ng/ml |
| B | 180 | 195.9 |
| C | 430 | 404.3 |
| D | 710 | 750.0 |

EXAMPLE 4

(1) Preparation of Biologically Active Composition

A plate for a carrier was prepared by using polystyrene according to the known polymer blend method.

Each 10 mg of poly-L-cysteine and poly-L-lysine was dissolved in a dimethyl sulfoxide-ether mixture solvent, and applied on the above plate. The solvent was then evaporated under reduced pressure. A micro phase separation between the poly-L-cysteine layer and the poly-L-lysine layer formed on the surface of the plate owing to the difference of condensation energy. When the SH groups content of the plate was measured by the dithiopyridone method and the amino groups content was measured by the ninhydrin method, the ratio of the SH groups to the amino groups was about 1:1. This polystyrene plate was cut into a square of 0.8 cm, and used as the carrier plate.

70 mg of bromoacetic acid and 115 mg of N-hydroxysuccinimide were dissolved in 4 ml of dioxane. 115 mg of dicyclohexylcarbodiimide was added to the solution, and allowed to react at room temperature for 90 minutes. The Dicyclohexyl urea thus formed was removed by filtering, and 0.1M sodium phophate buffer solution pH 7.5 was added to the filtrate until the volume was 25 ml. The above carrier plate was added to the filtrate, and allowed to react at 4° C. for 60 minutes. The plate was washed with 2 l of 0.1M NaCl and the bromoacetamide plate was obtained. This plate was immersed in 0.1M potassium phosphate buffer solution pH 6.0 containing 0.01M pyridoxal-5'-phosphate and 0.1M DL-valine, and allowed to stand at room temperature for 72 hours in a dark room. The plate was then washed at pH 9.0 and pH 5.5 with 0.1M potassium phosphate buffer solutions, and immersed in the same buffer solution of pH 7.0 to obtain the immobilized pyridoxal-5'-phosphate plate.

5 mg of goat anti human IgG specific IgG ($\alpha$-hIgG) was dissolved in 1 ml of 0.1M phosphate buffer solution pH 6.3. 100 $\mu$l of 2 mg/ml CHMS dioxane solution was added to the solution, and allowed to react at room temperature for 1 hour. The reaction mixture was introduced into a Sephadex G-25 column, and gel filtration was carried out by using 0.1M phosphate buffer solution pH 6.5 containing 1 mM EDTA to remove unreacted CHMS. The CHM induced $\alpha$-hIgG thus produced was added to the above immobilized pyridoxal-5'-phosphate plate, and allowed to react at 4° C. for 3 days. After the reaction, 0.05M phosphoric acid—0.14M NaCl buffer solution containing 5% BSA was added to the plate, and allowed to stand at 4° C. overnight to obtain the biologically active composition.

(2) Preparation of Combination Material 5 mg of human IgG (hIgG) was dissolved in a 0.1M phosphate buffer solution pH 7.5 containing 5 mM EDTA. 100 $\mu$l of 9 mg/ml S-acetylmercaptosuccinic anhydride dimethyl sulfoxide solution was added to the solution, and warmed at 37° C. for 1 hour. 110 $\mu$l of 1M hydroxylamine solution pH 7.5 was added to the mixture, and allowed to react at 37° C. for 30 minutes. The reaction mixture was introduced into a Sephadex G-25 column, and gel filtration was carried out by using 0.1M phosphate buffer solution at a pH 6.5 containing 1 mM EDTA to remove unreacted S-acetylmercaptosuccinic acid. Then, the reaction mixture was concentrated to 1 ml, and hIgG induced mercaptyl group was obtained.

On the other hand, 4 mg of G6PDH was dissolved in 1 ml of 0.1M phosphate buffer solution pH 6.3. 100 $\mu$l of 2 mg/ml CHMS dioxane solution was added to the solution, and allowed to stand at room temperature for 1 hour. The solution was then introduced into a Sephadex G-25 column, and unreacted CHMS was removed by gel filtration using 0.1M phosphate buffer solution pH 6.5 containing 1 mM EDTA. The above hIgG induced mercaptyl group was added to the CHM induced G6PDH thus obtained, and allowed to react at 4° C. overnight. As to the reaction mixture, gel filtration was carried out by using a Sephacryl S-300 column, and the G6PDH-hIgG combination material was obtained.

(3) Measurement of Human IgG

Each 50 $\mu$l of human IgG solution having various concentrations was placed in a test tube, and each 450 $\mu$l of the above combination matter was added. Subsequently, the above biologically active composition was added to each test tube and allowed to react at room temperature for 1 hour. Each 50 $\mu$l of 0.01% sodium borohydride aqueous solution was added to the test tube, and allowed to react at room temperature for 20 minutes.

The biologically active composition was taken out, and washed with a saline solution. The washed composition was placed in another test tube, and 1 ml of the substrate of G6PDH containing 0.1M glycylglycine buffer solution pH 8.5–20 mM MgCl$_2$, 0.5 mM G6P and 0.5 mM NADP was added to the test tube, and the absorbance at 340 nm was measured.

Figure 4:
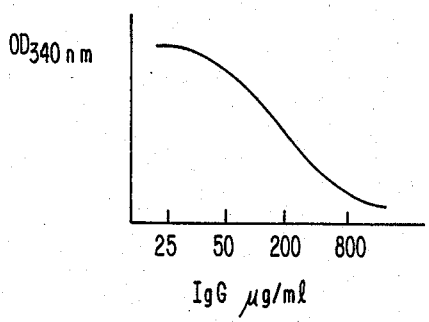

The results are shown in FIG. 4.

EXAMPLE 5

(1) Preparation of Biologically Active Composition

A solution of $\alpha$-amylase derived from hog pancreas and a solution of goat anti human IgE specific IgG were prepared in 30 mM sodium citrate—0.3M NaCl buffer solution so that OD$_{280}$ of the solution was 0.4, and a piece of filter paper was immersed in one each of the above solutions. The pieces of wet filter paper was superposed on a nitrocellulose membrane filter of 15×15 cm (made by Toyo Filter Paper Co., Ltd.), and allowed to stand at 4° C. for 2 days and thereby the $\alpha$-amylase and the IgG were separately adsorbed on the individual membrane filters. Each filter was immersed in 5% BSA—0.1M phosphate—0.14M NaCl pH 7.5 solution, and allowed to stand at 4° C. overnight. The filters were washed with 50 mM phosphate—0.14M NaCl pH 7.5, and dried under a vacuum at 4° C. Each dried filter was cut into the size of 0.5×0.75 cm, and stuck on both sides of an end of triacetate film having the size of 0.5×5×0.05 cm by using an adhesive of a vinyl compound so that the adsorption faces were on the outside. It was used as the biologically active composition.

(2) Preparation of Combination Material

CHM was induced to a human IgE separated from the serum of a myeloma patient according to the same method as employed in the case of AFP of Example 3, and the amylase inhibitor induced mercaptyl group prepared according to the same method as employed in Example 3 was added to this CHM induced human IgE to produce the combination material of IgE-amylase inhibitor. This combination material was purified by means of gel filtration using a Sephacryl S-300 column of 2×100 cm.

(3) Measurement of IgE

Each 50 $\mu$l of an IgE solution having various IgE concentrations was placed in a test tube, and each 450 $\mu$l of the above combination matter solution dissolved in 50 mM phosphate—0.14M NaCl—2% BSA solution was added. Subsequently, the above biologically active composition was placed in this test tube, and allowed to react at room temperature for 1 hour. After the reaction, the biologically active composition was taken out, and placed into another test tube in which 1 ml of enzyme substrate solution ("Autopack $\alpha$-Amylase", manufactured by Boehringer Mannheim GmbH) was added, and the absorbance at 405 nm after 10 minutes was measured to obtain the relation of the amount of IgE and the amylase activity.

Figure 5:
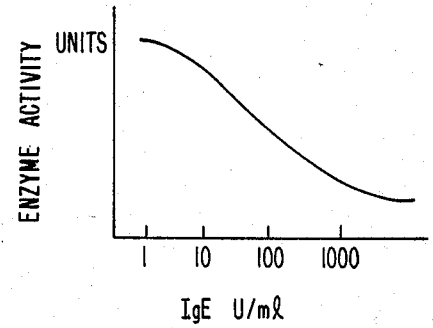

The results are shown in FIG. 5.

We claim:

1. A method of measuring the amount of an antigen which comprises the steps of:
   (a) forming a biologically active composition by:
       (i) immobilizing on a first solid phase an antibody capable of reacting with the antigen to be measured,
       (ii) immobilizing on a second solid phase a member selected from the group consisting of enzymes, enzyme inhibitors and enzyme activators; and wherein said first and second immobilized solid phases are separated from each other,
   (b) contacting said biologically active composition with an aqueous solution of a water soluble combination material and a solution of the antigen to be measured, said water soluble combination material comprised of an antigen capable of reacting with the first immobilized phase antibody, coupled with a member capable of reacting with the second immobilized phase selected from the group consisting of enzyme inhibitors, enzyme activators and enzymes with the proviso (a) that when the member immobilized on the second phase in (ii) is an enzyme, then the member of the water soluble combination material capable of reacting with the second immobilized phase is either an enzyme activator or an enzyme inhibitor and (b) that when the member immobilized on the second phase in (ii) is an enzyme activator or an enzyme inhibitor, then the member of the water soluble combination material capable of reacting with the second immobilized phase is an enzyme; and
   (c) measuring enzyme activity, enzyme inhibiting activity, or enzyme activating activity of the biologically active composition or solution.

2. A method of measuring the amount of an antigen which comprises the steps of:
   (a) forming a biologically active composition by:
       (i) immobilizing on a first solid phase an antigen capable of reacting with an antibody contained in an aqueous solution of a water soluble combination material,
       (ii) immobilizing on a second solid phase a member selected from the group consisting of enzymes, enzyme inhibitors and enzyme activators; and wherein said first and second immobilized solid phases are separated from each other,
   (b) contacting said biologically active composition with the aqueous solution of the water soluble combination material and a solution of the antigen to be measured, said water soluble combination material comprised of an antibody capable of reacting with the antigen of the first immobilized phase and the antigen to be measured, coupled with a member capable of reacting with the second immobilized phase selected from the group consisting of enzyme inhibitors, enzyme activators and enzymes with the proviso (a) that when the member immobilized on the second phase in (ii) is an enzyme, then the member of the water soluble combination material capable of reacting with the second immobilized phase is either an enzyme activator or an enzyme inhibitor and (b) that when the member immobilized on the second phase in (ii) is an enzyme activator or an enzyme inhibitor, then the member of the water soluble combination material capable of reacting with the second immobilized phase is an enzyme; and
   (c) measuring enzyme activity, enzyme inhibiting activity, or enzyme activating activity of the biologically active composition or solution.

3. The method of claim 2 wherein the antigen to be measured and the antigen capable of reacting with the antibody are the same.

4. The method of claim 3 wherein the antigen is obtained from an organ, blood or urine.

5. A method of measuring the amount of an antibody which comprises the steps of:
   (a) forming a biologically active composition by:
       (i) immobilizing on a first solid phase an antigen capable of reacting with the antibody to be measured,
       (ii) immobilizing on a second solid phase a member selected from the group consisting of enzymes, enzyme inhibitors and enzyme activators; and wherein said first and second immobilized solid phases are separated from each other,
   (b) contacting said biologically active composition with an aqueous solution of a water soluble combination material and a solution of the antibody to be measured, said water soluble combination material comprised of an antibody capable of reacting with the first immobilized phase antigen, coupled with a member capable of reacting with the second immobilized phase selected from the group consisting of enzyme inhibitors, enzyme activators and enzymes with the proviso (a) that when the member immobilized on the second phase in (ii) is an enzyme, then the member of the water soluble combination material capable of reacting with the second immobilized phase is either an enzyme activator or an enzyme inhibitor and (b) that when the member immobilized on the secod phase in (ii) is an enzyme activator or an enzyme inhibitor, then the member of the water soluble combination material capable of reacting with the second immobilized phase is an enzyme; and
   (c) measuring enzyme activity, enzyme inhibiting activity, or enzyme activating activity of the biologically active composition or solution.

6. A method of measuring the amount of an antibody which comprises the steps of:
   (a) forming a biologically active composition by:
       (i) immobilizing on a first solid phase an antibody capable of reacting with an antigen contained in an aqueous solution of a water soluble combination material,
       (ii) immobilizing on a second solid phase a member selected from the group consisting of enzymes, enzyme inhibitors and enzyme activators; and wherein said first and second immobilized solid phases are separated from each other,
   (b) contacting said biologically active composition with the aqueous solution of the water soluble combination material and a solution of the antibody to be measured, said water soluble combination material comprised of an antigen capable of reacting with the antibody of the first immobilized phase and the antibody to be measured, coupled with a member capable of reacting with the second immobilized phase selected from the group consisting of enzyme inhibitors, enzyme activators and enzymes with the proviso (a) that when the member immobilized on the second phase in (ii) is an enzyme, then the member of the water soluble combination material capable of reacting with the second immobilized phase is either an enzyme activator or an enzyme inhibitor and (b) that when the member immobilized on the second phase in (ii) is an enzyme activator or an enzyme inhibitor, then the member of the water soluble combination material capable of reacting with the second immobilized phase is an enzyme; and (c) measuring enzyme activity, enzyme inhibiting activity, or enzyme activating activity of the biologically active composition or solution.

7. The method of claim 2, 5 or 6 wherein the second immobilized solid phase comprises an enzyme or enyzme inhibitor and said water soluble combination comprises an enzyme inhibitor or enzyme capable of reacting with the second immobilized solid phase coupled with the antigen or antibody and the enzyme activity or enyzme inhibiting activity of the biologically active composition or the solution is measured.

8. The method of claim 7 wherein the enzyme activity is measured.

9. The method of claim 7 wherein the first immobilized phase antibody or water soluble combination material antibody is F(ab')$_2$, Fab', Fab or a second antibody against a first antibody.

10. The method of claim 7 wherein the enzyme is α-amylase, β-galactosidase or esterase.

11. The method of claim 7 wherein the enzyme is selected from the groups consisting of α-amylase, β-galactosidase and esterase and wherein the enzyme inhibitor is selected from the group consisting of α-amylase inhibitor, isoflavonoid and bestatin.

12. The method of claim 7 wherein the biologically active composition is a polymer on which the antigen or antibody and the enzyme or enzyme inhibitor are separately immobilized on parts of the same polymer particle.

13. The method of claim 12 wherein the polymer is a block-copolymer or a graft-copolymer.

14. The method of claim 7 wherein the biologically active composition comprises two polymer particles adhering to each other, on one of the polymer particles the antigen or antibody is immobilized and on the other polymer particle, the enzyme or enzyme inhibitor is immobilized.

15. The method of claim 7 wherein the biologically active composition comprises two separate particles on one of the particles the antigen or antibody is immobilized and on the other particle the enzyme or enzyme inhibitor is immobilized.

16. The method of claim 1 or 2 wherein the antigen to be measured is obtained from an organ, blood or urine.

17. The method of claim 16 wherein the antigen to be measured is a hormone derived from an endocrine gland, a blood serum protein, an immune complex, a pathogen, a complement, a drug, a cyclic nucleotide, an α-fetoprotein or a carcinoembryonic antigen.

18. The method of claim 17 wherein the antigen to be measured is ferritin, $\beta_2$-microglobulin, α-fetoprotein, human IgG or human IgE.

* * * * *